US007207913B2

(12) United States Patent
Gebrian

(10) Patent No.: US 7,207,913 B2
(45) Date of Patent: Apr. 24, 2007

(54) BI-DIRECTIONAL DRIVEBELT TENSIONING DEVICE

(75) Inventor: Peter Louis Gebrian, Wilmington, DE (US)

(73) Assignee: Dade Behring Inc., Deerfield, IL (US)

( * ) Notice: Subject to any disclaimer, the term of this patent is extended or adjusted under 35 U.S.C. 154(b) by 263 days.

(21) Appl. No.: 10/623,311

(22) Filed: Jul. 18, 2003

(65) Prior Publication Data

US 2005/0014588 A1 Jan. 20, 2005

(51) Int. Cl.
*F16H 7/12* (2006.01)

(52) U.S. Cl. ........................................ 474/138

(58) Field of Classification Search ............... 474/101, 474/109, 113, 136, 138
See application file for complete search history.

(56) References Cited

U.S. PATENT DOCUMENTS 4,300,890 A * 11/1981 Hallmann et al. .......... 474/110
4,457,741 A * 7/1984 Hoeptner, III .............. 474/138
4,464,147 A * 8/1984 Foster ........................ 474/135
4,834,694 A 5/1989 Martin ....................... 474/135
4,883,446 A 11/1989 Mitchell et al. ............ 474/133
4,914,984 A 4/1990 Fub et al. ...................... 74/867
5,030,173 A 7/1991 Bryant
5,098,347 A 3/1992 Sajczvk et al. ............. 474/135
5,131,889 A 7/1992 Mechstroth et al. ........ 474/117
5,152,721 A 10/1992 Sajczvk et al. ............. 474/135
5,256,113 A 10/1993 Bushman et al. ........... 474/135
5,277,666 A 1/1994 Kumm ....................... 474/133
5,312,302 A 5/1994 Yamamoto .................. 474/135
5,352,160 A 10/1994 Sakai et al. ................. 474/117
5,439,420 A 8/1995 Mechstroth et al. ........ 474/133
5,540,627 A 7/1996 Miyata ....................... 474/112
5,752,891 A 5/1998 Mechstroth et al. ........ 474/110
5,782,625 A 7/1998 Young
5,803,849 A 9/1998 Ayukawa ..................... 474/94
5,967,923 A 10/1999 Petri .......................... 474/138
6,159,120 A * 12/2000 Rointru et al. .............. 474/138
6,364,236 B1 4/2002 Fohl ........................... 242/374
6,458,055 B1 10/2002 Bellamy-Booth ........... 474/135
6,485,207 B1 11/2002 Allen et al.
6,592,482 B2 7/2003 Serkh ......................... 474/135
6,607,459 B1 8/2003 Serkh et al.

* cited by examiner

*Primary Examiner*—Vicky A. Johnson
(74) *Attorney, Agent, or Firm*—Leland K. Jordan

(57) ABSTRACT

A device for automatically maintaining tension and control of a drivebelt as the driving direction of the drivebelt is rapidly reversed and when the drivebelt is worn.

1 Claim, 10 Drawing Sheets

80
82
86
86S
89
90
87
86F
85
84

70
64
72
74
30
68
76
66

66
78
80
86
83
84
87
82
81
85
87
81

90
85
89
84
86
86S
82
80

86F
87

BI-DIRECTIONAL DRIVEBELT TENSIONING DEVICE

FIELD OF THE INVENTION

The present invention relates to a method and apparatus for automatically processing a patient's biological fluids such as urine, blood serum, plasma, cerebrospinal fluid and the like. In particular, the present invention provides a device for automatically maintaining tension and control of a drivebelt as the driving direction of the drivebelt is rapidly reversed and when the drivebelt is worn.

BACKGROUND OF THE INVENTION

Various types of tests related to patient diagnosis and therapy can be performed by analysis of a sample of a patient's infection, bodily fluid or abscess for an analyte of interest. Patient samples are typically placed in sample vials, the vials transported to a clinical laboratory, placed into racks on an automated clinical analyzer and sample is extracted from the vials. Subsequently, samples are combined in reaction vessels with various reagents extracted from reagent cartridges; the mixture is possibly incubated before being analyzed to aid in treatment of the patient. Interrogating measurements, turbidimetric or fluorometric or the like, are made to ascertain end-point or reaction rate values from which the amount of analyte in the sample may be determined, using well-known calibration techniques.

Automated clinical analyzers improve operating efficiency by providing results more rapidly while minimizing operator or technician error. Due to increasing demands on clinical laboratories regarding assay throughput, the efficiency of handling patient samples and reagents within an analyzer continually needs to be increased, and an important factor is the ability to quickly position a plurality of different samples or reagents at an appropriate liquid extraction location.

The sample rack is usually placed by an operator in an input portion of the analyzer and automatically moved by the analyzer to an aliquotting location where an aliquot of the liquid patient sample is extracted, usually by aspiration using a hollow probe from the sample container. Aliquot samples from a number of different patient samples may be dispensed into a plurality of interim vessels or wells formed as an integral array of small open cup-like vessels, herein called an aliquot vessel array, like that described in U.S. patent Ser. No. 10/037,512, assigned to the assignee of the present invention. Aliquot vessel arrays are transported to a sampling location where an appropriate amount of the aliquot sample is extracted by a sampling probe and dispensed by a sampling probe into a reaction cuvette. In addition, reagent(s) required to conduct specified assays are extracted at a reagenting location from appropriate reagent cartridge(s) using hollow probes that are subsequently shuttled to a reagent dispensing location where reagent(s) are dispensed into the reaction cuvette.

In order to maintain high assay throughput, it is advantageous that sampling probes be quickly shuttled between sampling locations and reaction cuvettes and that reagenting probes be quickly shuttled between reagenting locations and reaction cuvettes. It is also advantageous that reagent cartridges be quickly shuttled between on-board storage locations and reagenting locations. In all of these shuttling and positioning operations, it is desirable that the aliquot vessel arrays, reagent cartridges, sampling probes, and reagenting probes be accurately and repeatably positioned at their selected locations. Motorized drivebelts are frequently employed in shuttling operations like described, however the drivebelts are known to stretch from their original dimensions in long term repeated use making it difficult to repeatably position a probe or cartridge or the like at its intended location. Furthermore, when the direction of travel of a drivebelt is rapidly reversed, the drivebelt may dislodge from an associated pulley and belt or sprocket and chain unless it is maintained at a tension of sufficient strength.

SUMMARY OF THE INVENTION

The present invention provides a device to automatically compensate for unknown changes in length of a drivebelt by maintaining a constant tension on a drivebelt regardless of rapid changes in its driving direction so that probes or cartridges or the like may be accurately positioned at their intended location as the drivebelt wears. Such an automatic tensioning device employs a uni-directional latching device adapted to allow a belt-driven tensioner to move only in the direction that increases the distance between the tensioner and the driving source of the driving belt. As the driving belt increases length, a constant tension is maintained thereon.

BRIEF DESCRIPTION OF THE DRAWINGS

The invention will be more fully understood from the following detailed description thereof taken in connection with the accompanying drawings which form a part of this application and in which.

DETAILED DESCRIPTION OF THE INVENTION

Figure 1:
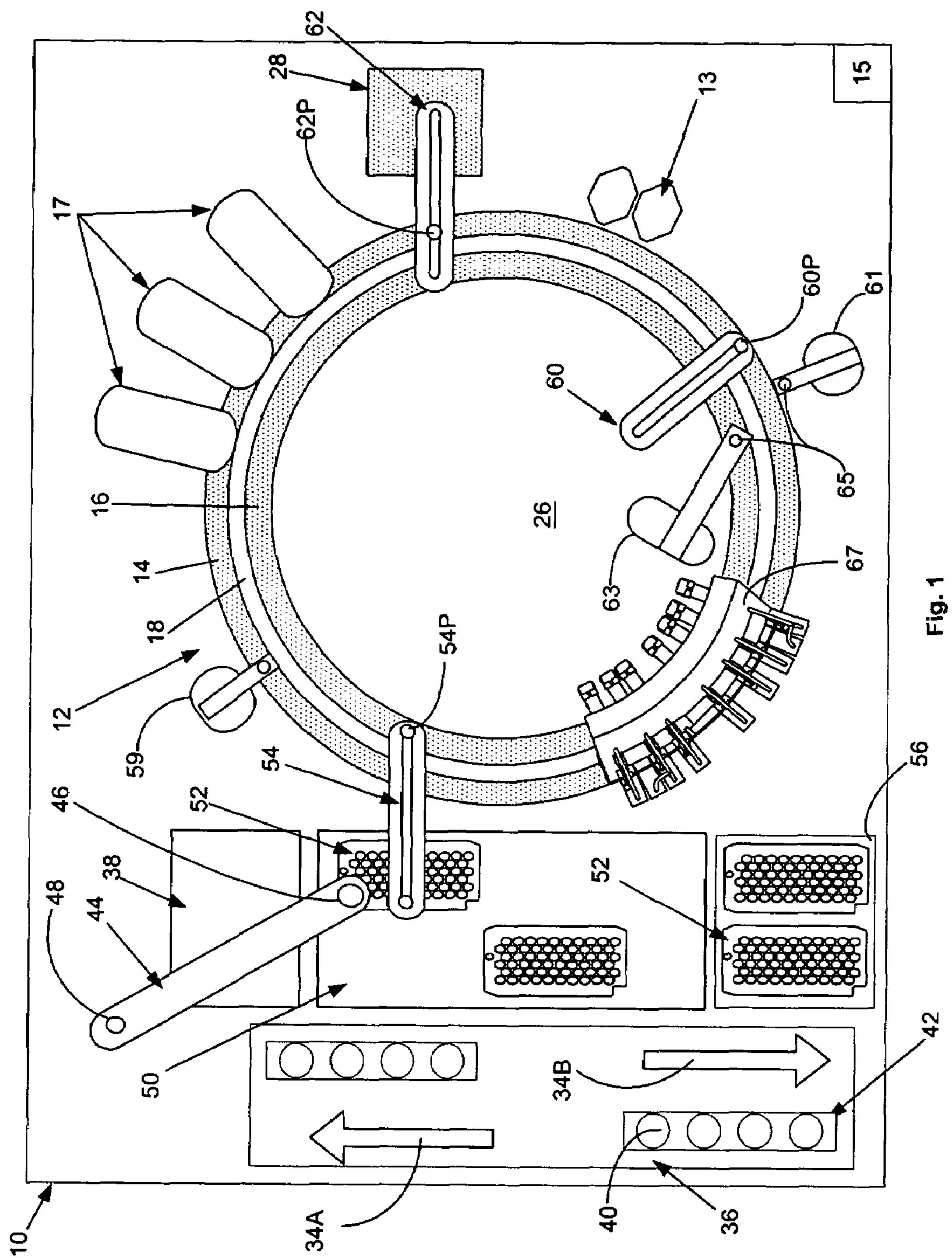
FIG. 1 is a schematic plan view of an automated analyzer in which the present invention may be employed to advantage.
Figure 2:
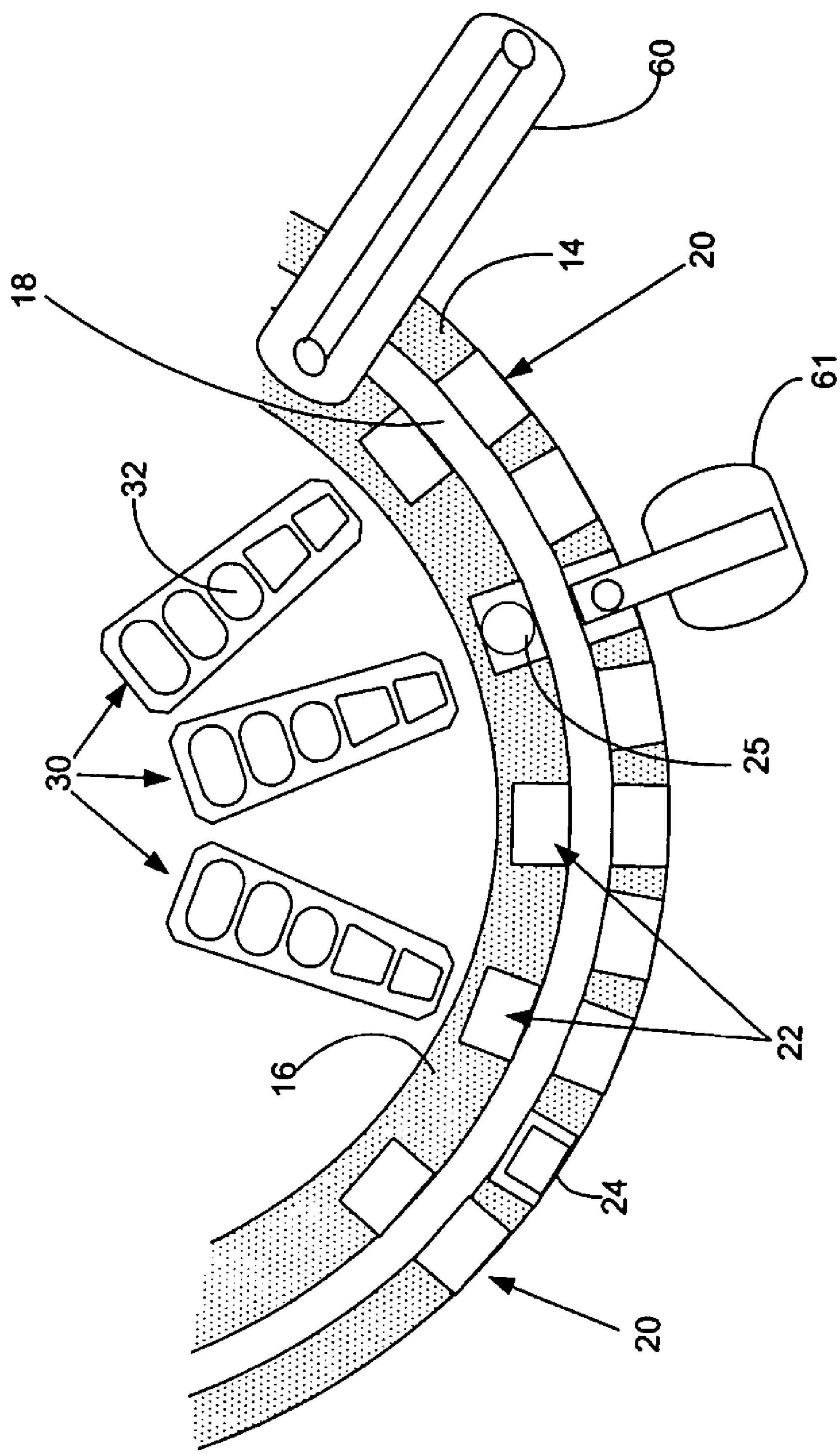
FIG. 2 is an enlarged schematic plan view of a portion of the analyzer of FIG. 1.

FIG. 1, taken with FIG. 2, shows schematically the elements of an automatic chemical analyzer 10 in which the present invention may be advantageously practiced, analyzer 10 comprising a reaction carousel 12 supporting an outer cuvette carousel 14 having cuvette ports 20 formed therein and an inner cuvette carousel 16 having vessel ports 22 formed therein, the outer cuvette carousel 14 and inner cuvette carousel 16 being separated by a open groove 18. Cuvette ports 20 are adapted to receive a plurality of reaction cuvettes 24 like disclosed in co-pending application Ser. No. 10/623,436 assigned to the assignee of the present invention and containing various reagents and sample liquids for conventional clinical and immunoassay assays while vessel ports 22 are adapted to receive a plurality of reaction vessels 25 that contain specialized reagents for ultra-high sensitivity luminescent immunoassays. Reaction carousel 12 is rotatable using stepwise movements in a constant direction, the stepwise movements being separated by a constant dwell time during which carousel 12 is maintained stationary and computer controlled assay operational devices 13, such as sensors, reagent add stations, mixing stations and the like, operate as needed on an assay mixture contained within cuvettes 24 and reaction vessels 25.

Analyzer 10 is controlled by software executed by the computer 15 based on computer programs written in a machine language like that used on the Dimension® clinical chemistry analyzer sold by Dade Behring Inc, of Deerfield, Ill., and widely used by those skilled in the art of computer-based electromechanical control programming. Computer 15 also executes application software programs for performing assays conducted by various analyzing means 17 within analyzer 10.

Temperature-controlled reagent storage areas 26 and 28 store a plurality of multi-compartment elongate reagent cartridges 30 like that described in co-pending application Ser. No. 09/949,132 assigned to the assignee of the present invention, and containing reagents in wells 32 as necessary to perform a given assay.

A bi-directional incoming and outgoing sample tube transport system 36 having input lane 34A and output lane 34B transports incoming individual sample tubes 40 containing liquid specimens to be tested and mounted in sample tube racks 42 into the sampling arc of a liquid sampling arm 44. Liquid specimens contained in sample tubes 40 are identified by reading bar coded indicia placed thereon using a conventional bar code reader to determine, among other items, a patient's identity, the tests to be performed, if a sample aliquot is to be retained within analyzer 10 and if so, for what period of time. It is also common practice to place bar coded indicia on sample tube racks 42 and employ a large number of bar code readers installed throughout analyzer 10 to ascertain, control and track the location of sample tubes 40 and sample tube racks 42.

Figure 3:
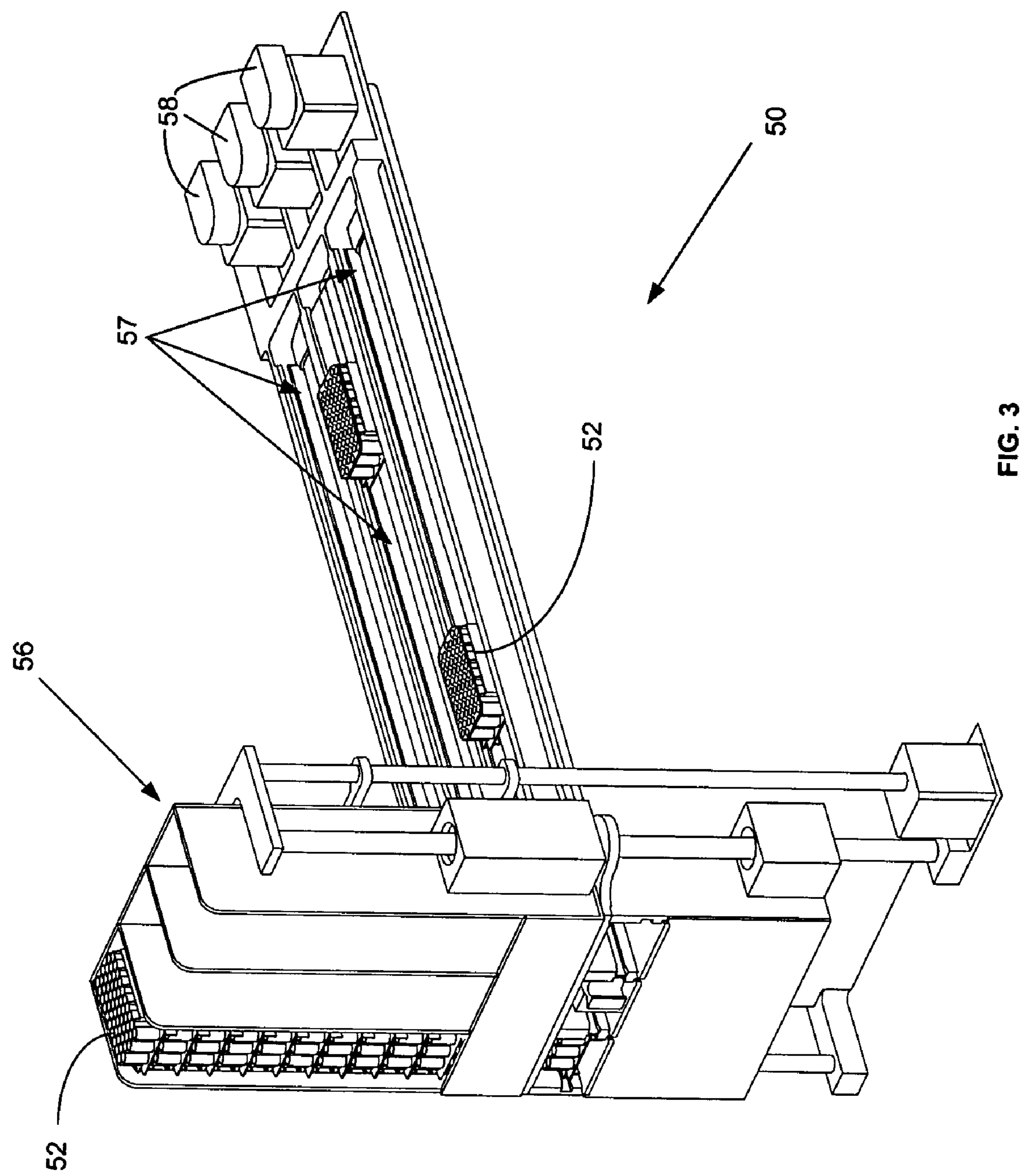
FIG. 3 is a perspective elevation view of an automated aliquot vessel array storage and handling unit.
Figure 4:
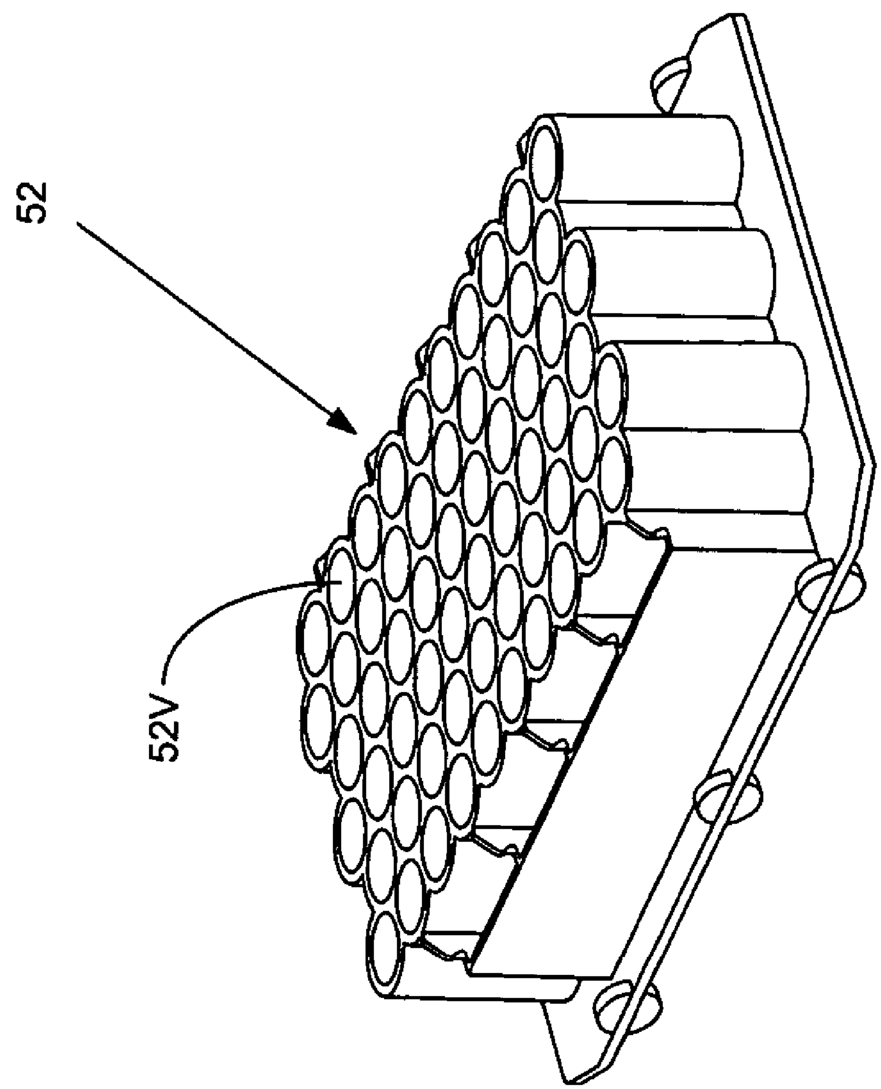
FIG. 4 is a perspective elevation view of an aliquot vessel array.

Sampling arm 44 supports a liquid sampling probe 46 mounted to a rotatable shaft 48 so that movement of sampling arm 44 describes an arc intersecting the sample tube transport system 36 and an aliquot vessel array transport system 50, as seen in FIG. 3. Sampling arm 44 is operable to aspirate liquid sample from sample tubes 40 and to dispense an aliquot sample into one or more of a plurality of vessels 52V in aliquot vessel array 52, as seen in FIG. 4, depending on the quantity of sample required to perform the requisite assays and to provide for a sample aliquot to be retained by analyzer 10 within environmental chamber 38.

Aliquot vessel array transport system 50 comprises an aliquot vessel array storage and dispense module 56 and a number of linear drive motors 58 adapted to bi-directionally translate aliquot vessel arrays 52 within a number of aliquot vessel array tracks 57 below a sample aspiration and dispense arm 54 located proximate reaction carousel 12. Sample aspiration and dispense arm 54 is controlled by computer 15 and is adapted to aspirate a controlled amount of sample from individual vessels 52V positioned at a sampling location within a track 57 using a conventional liquid probe 54P and then liquid probe 54P is shuttled to a dispensing location where an appropriate amount of aspirated sample is dispensed into one or more cuvettes 24 in cuvette ports 20 for testing by analyzer 10 for one or more analytes. After sample has been dispensed into reaction cuvettes 24, conventional transfer means move aliquot vessel arrays 52 as required between aliquot vessel array transport system 50, environmental chamber 38 and a disposal area, not shown.

A number of reagent aspiration and dispense arms 60 and 62 comprising a pair of conventional liquid reagent probes, 60P and 62P, respectively, are independently mounted and translatable between reagent storage areas 26 and 28, respectively. Probes 60P and 62P comprise conventional mechanisms for aspirating reagents required to conduct specified assays at a reagenting location from wells 32 in an appropriate reagent cartridge 30, the probes 60P and 62P subsequently being shuttled to a reagent dispensing location where reagent(s) are dispensed into reaction cuvettes 24. A number of reagent cartridges 30 are inventoried in controlled environmental conditions inside reagent storage areas 26 and 28; a key factor in maintaining high assay throughput is the ability to quickly and accurately shuttle reagent cartridges 30 inside reagent storage areas 26 and 28 to reagenting locations for access by probes 60P and 62P.

Reaction cuvette load station 61 and reaction vessel load station 63 are respectively positioned proximate outer cuvette carousel 14 and inner vessel carousel 16 and are adapted to load reaction cuvettes 24 into cuvette ports 20 sideways as described later and reaction vessels 25 into vessel ports 22 using for example a translatable robotic arm 65. In operation, used cuvettes 24 in which an assay has been finally conducted, are washed and dried in a wash station 67 like disclosed in co-pending application Ser. No. 10/623,360 assigned to the assignee of the present invention. Subsequent assays are conducted in cleaned used cuvettes 24 unless dictated otherwise for reasons like disclosed in co-pending application Ser. No. 10/318,804 assigned to the assignee of the present invention. Cuvette unload station 59 is adapted to remove unusable reaction cuvettes 24 from cuvette ports 20 again using a translatable robotic arm 65 like seen on load stations 61 and 63.

A problem often encountered in the process of shuttling reagent cartridges 30 is that during use, the shuttling mechanism experiences wear adversely affecting the accuracy with which reagent cartridges 30 are presented to probes 60P and 62P. Another problem arises when abrupt reversals in the shuttling direction of reagent cartridges 30 are made at high speed because the change in load experienced by, for example, the driving or the slack portion of a circular drivebelt, causes reagent cartridges 30 to be stopped at gradually changing locations. The present invention is useful in a cartridge shuttle mechanism 64 like that shown in FIG. 5 and comprises an automated tensioner 66 to compensate for changes in length a shuttling chain or drivebelt 68 may experience during use or for changes in tension the drivebelt 68 may experience during abrupt reversals of direction so that probes 60P and 62P or cartridges 30 or the like may be accurately positioned at their intended location as the shuttling chain or drivebelt 68 wears.

Figure 5:
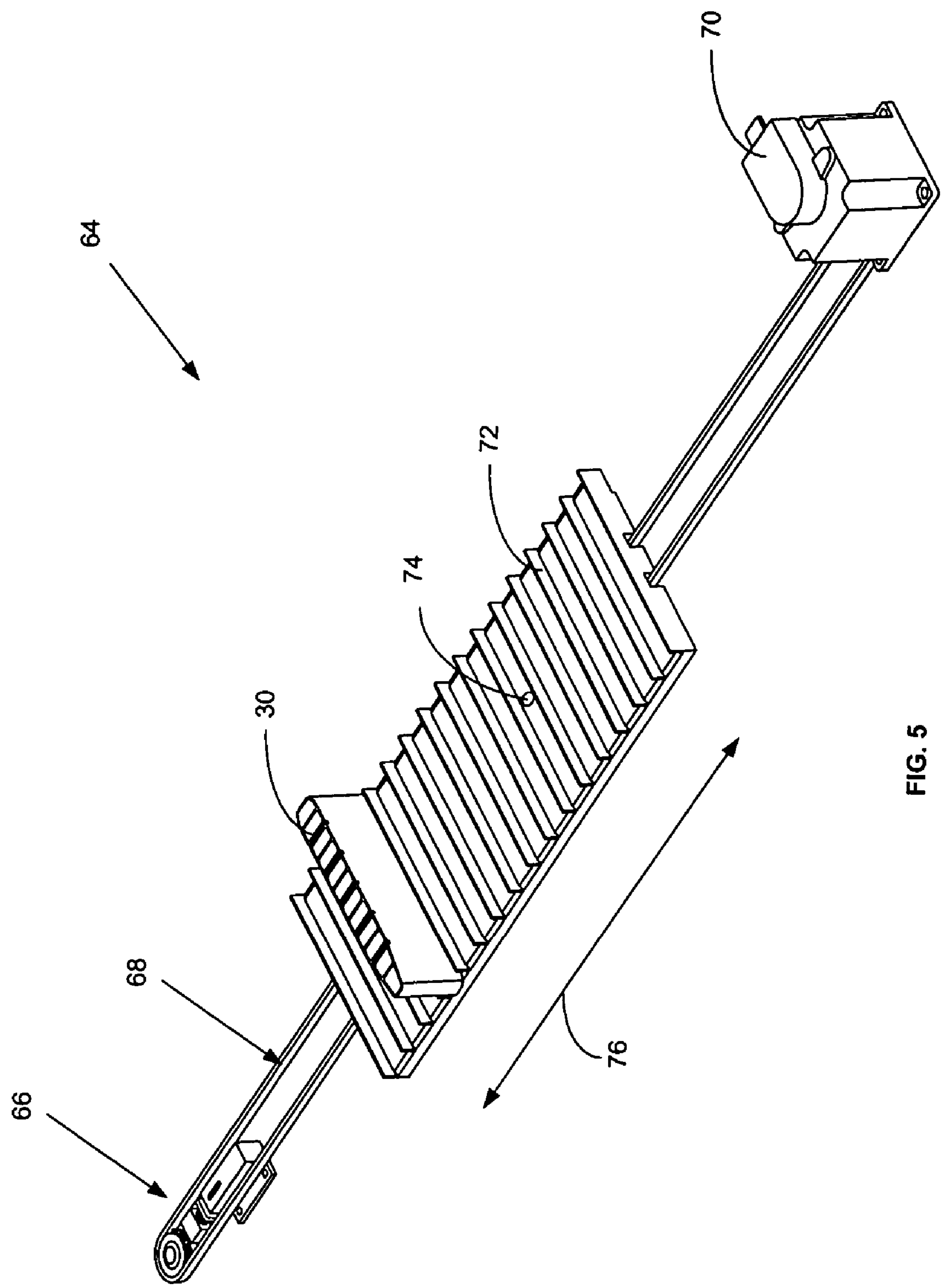
FIG. 5 is a perspective elevation view of a cartridge shuttle mechanism in which the present invention may be used to advantage.

In an exemplary use of automated tensioner 66 as shown in FIG. 5, motor 70 is controlled by computer 15 to circulate drivebelt 68 in clockwise and counter-clockwise directions, in order to position a cartridge carrier 72 having a number of reagent cartridges 30 secured thereon, only one reagent cartridge 30 being illustrated for purposes of simplicity.

Carrier 72 is shown schematically secured only on one side by tie-down 74 to only one leg of drivebelt 68 so that carrier 72 is free to be driven to and from along the direction of drivebelt 68, as indicated by double-ended arrow 76. Consequently, cartridge 30 may be positioned as desired at a reagenting location.

Figures 6A, 6B:
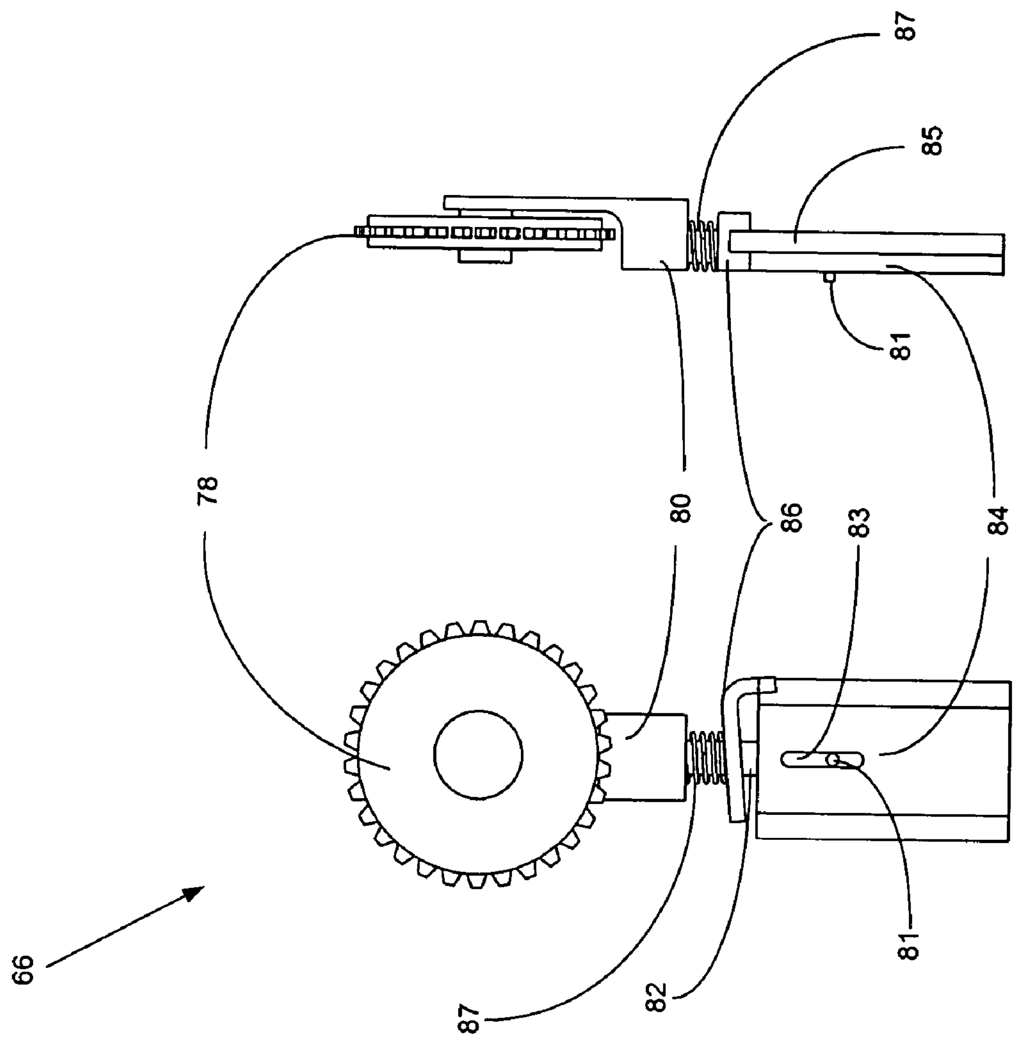
FIG. 6A is a front view of the automated tensioner of the present invention.
FIG. 6B is a side view of the automated tensioner of FIG. 6A.
Figure 7:
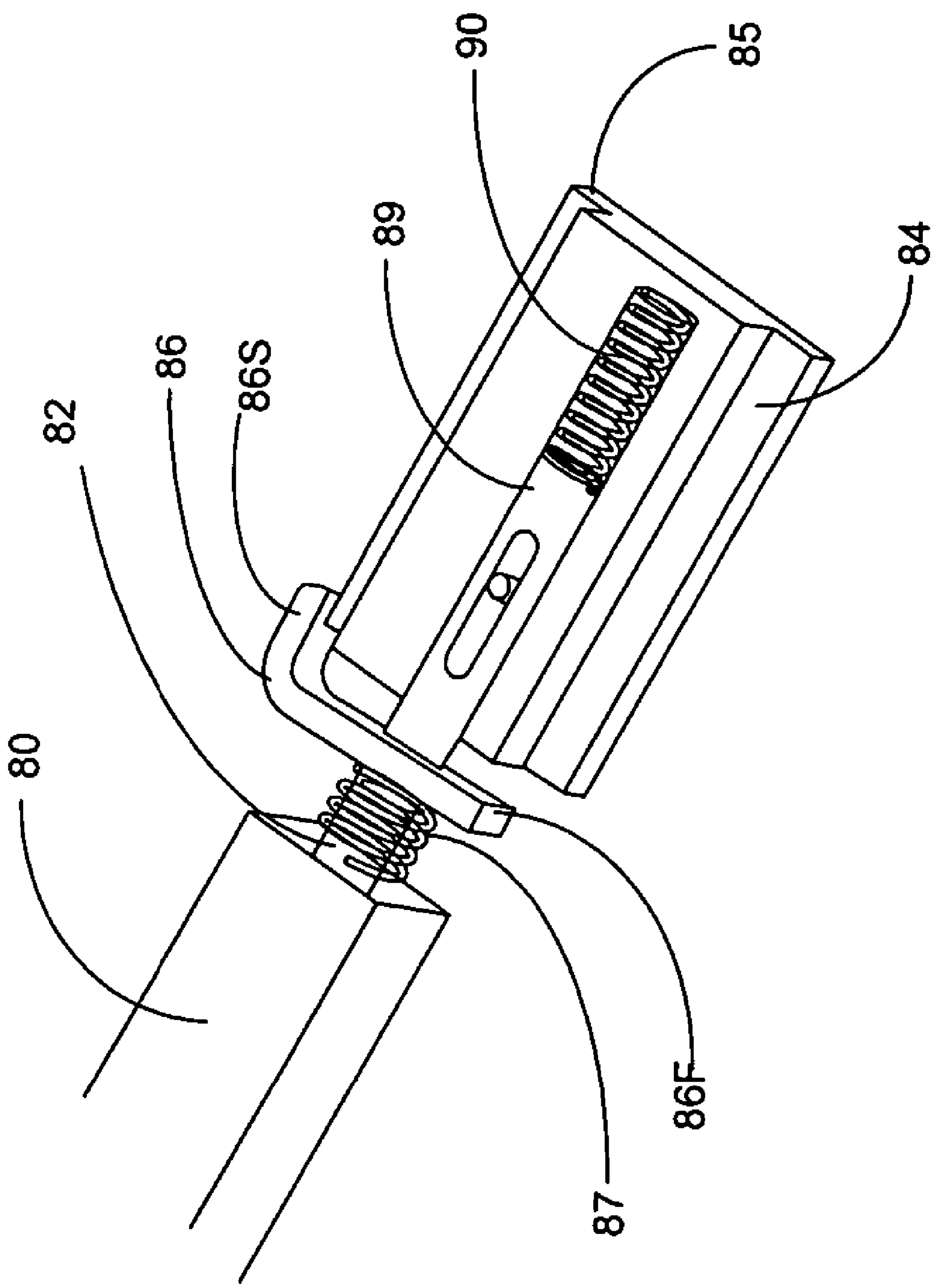
FIG. 7 is a perspective cut-away view of key features of the present invention.

FIG. 6A, a plan view, and FIG. 6B, a side view, show elements of automated tensioner 66 as comprising a sprocket 78 rotatably attached to a sprocket-arm 80, sprocket-arm 80 having a leg portion 82 slideably inserted within a closed end bore 89 (see FIG. 7) formed in latching base 84, leg portion 82 maintained in a plane via pin 81 slideable within groove 83 also formed in latching base 84. An important feature of tensioner 66 is an elongate latch 86 and latching spring 87, latch 86 having a latching porthole 88 (see FIG. 7B) formed in its central portion, leg portion 82 being slideably inserted therethrough. Elongate 86 has a gap 89 formed between prongs 91 (FIG. 7B) that fits over an extended ledge 85 (see FIG. 7) at the back of latching base 84.

Figure 7B:
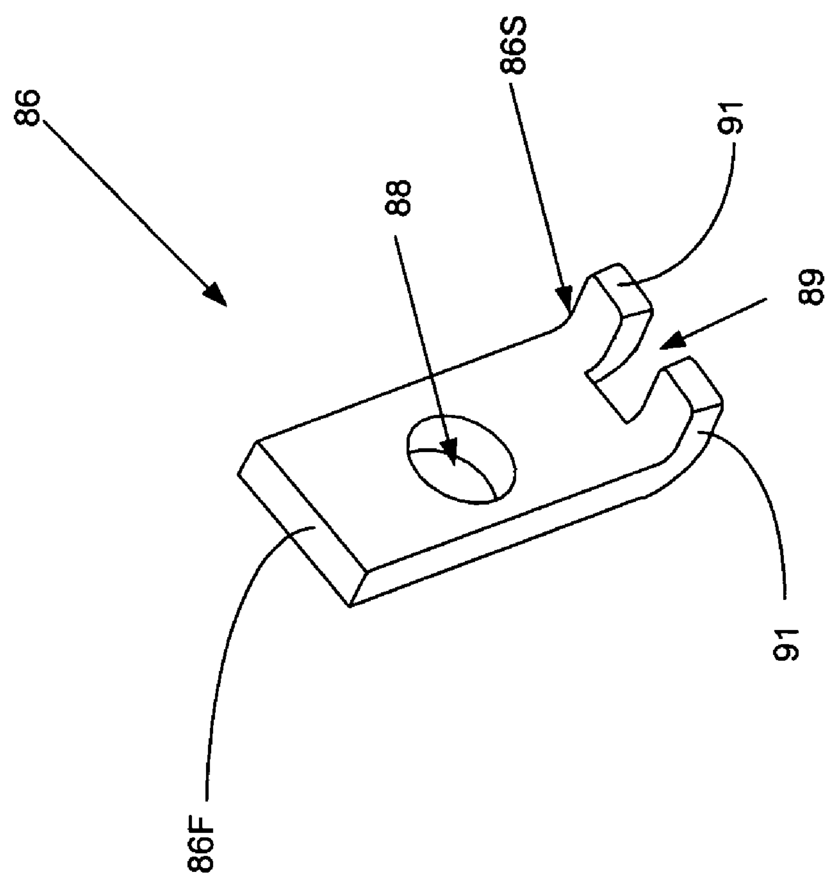
FIG. 7B is perspective view of a latch used within the present invention.
Figure 7A:
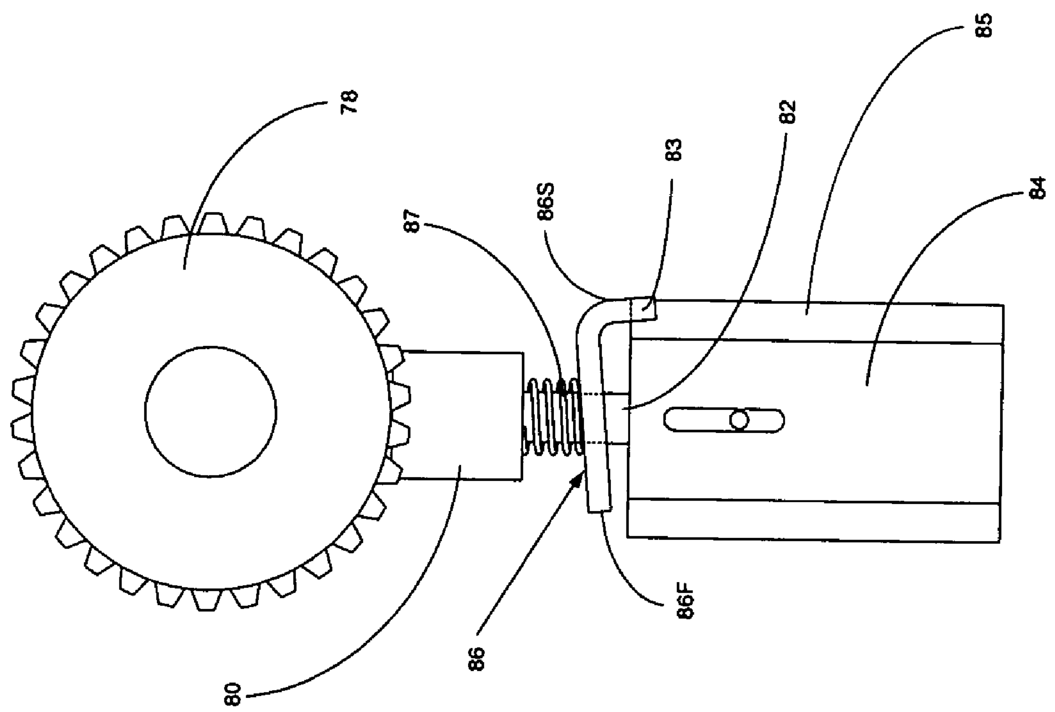
FIG. 7A is an enlarged front view of key features of the present invention.
Figure 8:
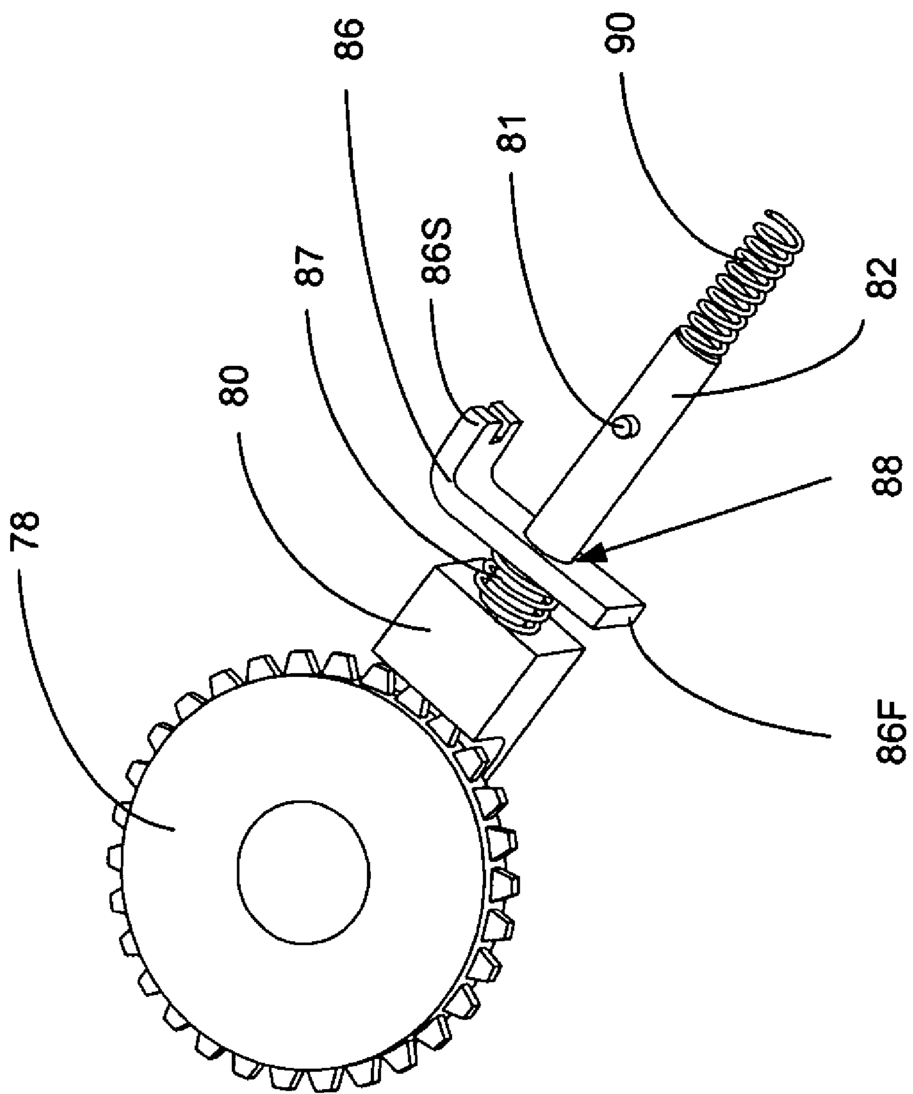
FIG. 8 is perspective view of key features of the present invention.

FIG. 7A is an enlarged view of latch 86 as gap 89 is positioned over ledge 85 of latching base 84, leg portion 82 inserted through latching porthole 88 and disposed within closed bore 89 (FIG. 7) also illustrating a latching spring 87 disposed between sprocket-arm 80 and latch 86; a compression spring 90 (FIG. 7) is also disposed between leg portion 82 and the end of closed bore 89. An important feature of the present invention is a freely hanging first end portion 86F adapted to cooperate with a second end portion 86S disposed in stationary contact with latching base 84. As best seen in FIG. 7A, due to the pressure exerted by latching spring 87 and the vertical freedom of first end portion 86F, latch 86, having leg portion 82 inserted through latching porthole 88, will assume a non-perpendicular relationship with leg portion 82 so that a latching interference is created between latching porthole 88 of latch 86 and leg portion 82. Consequently, in operation, latching spring 87 and latch 86 cooperate in a manner that allows sprocket-arm 80 to slide "away from" latching base 84 because a lower force within latching spring 87 "unlocks" or releases to allow movement between latch 86 and leg portion 82 but the latching interference between latching porthole 88 of and leg portion 82 prevents sprocket-arm 80 from moving in the opposite direction "toward" latching base 84. A unidirectional latching effect is thereby created by the combined latching spring 87 and latch 86 due to the presence of latching porthole 88 having leg portion 82 slideably inserted therethrough as is more clearly illustrated in FIG. 8.

FIG. 7B illustrates one embodiment of latch 86 and latching porthole 88 in which the stationary end 86S of latch 86 is bifurcated so that a gap 89 is formed between prongs 91, gap 89 being sized to fit over a projection 83 of latching base 84, best seen in FIG. 7A, thereby preventing rotation of latch 86 during use.

An important feature of the present invention is a compression spring 90 disposed between leg portion 82 and the end of closed bore 89 acting in a manner to constantly bias leg portion 82 within closed end bore 89 outwardly from the end of closed bore 89 causing tensioner 66 to automatically increase the separation of sprocket 78 relative to the location of motor 70 so that drivebelt 68 maintains a constant operating tension irregardless of abrupt changes in the direction of drivebelt 68 and under in-use wear that causes drivebelt 68 to lengthen. One skilled in the art will appreciate the advantage of the present invention in that it allows use of a high speed, light weight belt or drive chain at low operation tension in conjunction with a relatively smaller motor and relatively low belt tension in contrast to the use of large springs and low speed operation to achieve the same accurate positioning.

Figure 9:
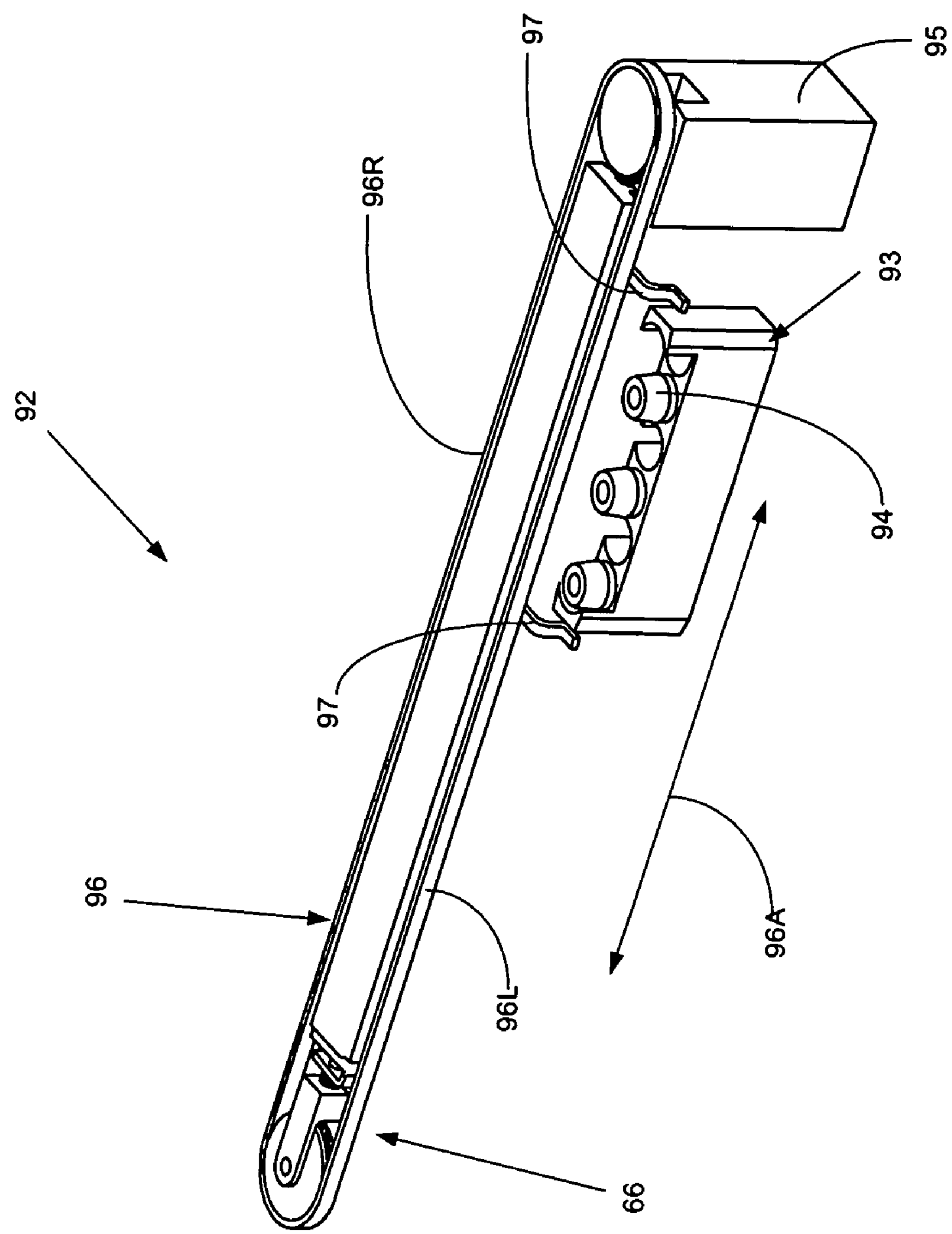
FIG. 9 is a perspective elevation view of a container shuttle mechanism in which the present invention may be used to advantage.

FIG. 9 is another application of the tensioner 66 of the present invention in a container shuttle mechanism 92 for shuttling an elongate container array 93 having a number of circular vials 94 having, for example, calibration solutions therein. Motor 95 is adapted to drive drivebelt 96 in clockwise and counter-clockwise directions, drivebelt 96 having container array 93 constrained between fingers 97 so that container array 93 is shuttled bi-directionally along double-headed arrow 96A. As in the instance of the previously described cartridge shuttle mechanism 64, FIG. 5, the load of the weight of container array 93 and the rapid reversals in the driving direction of drivebelt 96 cause the portion of drivebelt 96 designated 96R to alternate between having a taunt or loose tension, depending on whether the container array 93 is being shuttled towards or away from tensioner 66, respectively. Likewise, the portion of drivebelt 96 designated 96L will alternate between having a loose or taunt tension, depending on whether the container array 93 is being shuttled towards or away from tensioner 66, respectively. Again, in order that multiple aspirations of calibration solutions from vials 94 be made at a accurately positioned location, it is required that drivebelt 96 be maintained at the same operating tension during use. Wear and subsequent lengthening of drivebelt 96 during use must be taken into consideration and means provided to compensate therefor. As explained previously, tensioner 66 is adapted to automatically increase the separation of sprocket 78 relative to the location of motor 95 so that drivebelt 96 maintains a constant operating tension even if drivebelt 96 is caused to lengthen because of wear during use.

It will be appreciated by those skilled in that art that a number of design variations may be made in the above and still achieve the essence of the present invention. For example, the linearly actuated tensioner may alternatively be configured as an angularly displaced tensioner, employing the same latching mechanism. For these reasons, the present invention is not limited to those embodiments precisely shown and described in the specification but only by the following claims.

I claim:

1. An automated tensioner comprising a sprocket or pulley rotatably attached to an arm, the arm having an integral leg portion slideable within a closed end bore formed in a latching base, the leg portion slideable away from the base and prevented from moving towards the base through a latching porthole in an elongate latch, wherein said leg portion has a pin protruding therefrom, the pin disposed slideably within a groove formed in the latching base.

* * * * *